US006964680B2

(12) United States Patent
Shanley

(10) Patent No.: US 6,964,680 B2
(45) Date of Patent: Nov. 15, 2005

(54) EXPANDABLE MEDICAL DEVICE WITH TAPERED HINGE

(75) Inventor: John F. Shanley, Redwood City, CA (US)

(73) Assignee: Conor Medsystems, Inc., Menlo Park, CA (US)

( * ) Notice: Subject to any disclaimer, the term of this patent is extended or adjusted under 35 U.S.C. 154(b) by 19 days.

(21) Appl. No.: 10/057,414

(22) Filed: Jan. 25, 2002

(65) Prior Publication Data

US 2002/0107563 A1  Aug. 8, 2002

Related U.S. Application Data

(60) Provisional application No. 60/266,805, filed on Feb. 5, 2001.

(51) Int. Cl.[7] ............................................. A61F 2/06
(52) U.S. Cl. ..................................................... 623/1.15
(58) Field of Search ................................. 623/1.15, 1.2, 623/1.17, 1.18

(56) References Cited

U.S. PATENT DOCUMENTS

| | | |
|---|---|---|
| 3,657,744 A | 4/1972 | Ersek |
| 4,300,244 A | 11/1981 | Bokros |
| 4,531,936 A | 7/1985 | Godon |
| 4,542,025 A | 9/1985 | Tice et al. |
| 4,580,568 A | 4/1986 | Gianturco |
| 4,650,466 A | 3/1987 | Luther |
| 4,733,665 A | 3/1988 | Palmaz |
| 4,733,665 A | 3/1988 | Palmaz |
| 4,739,762 A | 4/1988 | Palmaz |
| 4,739,762 A | 4/1988 | Palmaz |
| 4,776,337 A | 10/1988 | Palmaz |
| 4,776,337 A | 10/1988 | Palmaz |
| 4,800,882 A | 1/1989 | Gianturco |
| 4,824,436 A | 4/1989 | Wolinsky |
| 4,834,755 A | 5/1989 | Silvestrini et al. |
| 4,955,878 A | 9/1990 | See et al. |
| 4,957,508 A | 9/1990 | Kaneko et al. |
| 4,960,790 A | 10/1990 | Stella et al. |
| 4,969,458 A | 11/1990 | Wiktor |
| 4,989,601 A | 2/1991 | Marchosky et al. |
| 4,990,155 A | 2/1991 | Wilkoff |
| 4,994,071 A | 2/1991 | MacGregor |
| 5,019,090 A | 5/1991 | Pinchuk |

(Continued)

FOREIGN PATENT DOCUMENTS

CA    2234787    4/1998

(Continued)

OTHER PUBLICATIONS

Emanelsson, et al., "The Jostent Coronary Stent Range", Chapter 19.

(Continued)

*Primary Examiner*—Michael Thaler
(74) *Attorney, Agent, or Firm*—Cindy A. Lynch

(57) ABSTRACT

According to the present invention there is provided an expandable medical device having, a plurality of elongated beams, the plurality of elongated beams joined together to form a substantially cylindrical device which is expandable from a cylinder having a first diameter to a cylinder having a second diameter. A plurality of hinges connecting the elongated beams have a hinge width, wherein the hinge width is smaller than the beam width. A pawl is disposed adjacent to and substantially parallel to the hinge prior to expansion of the medical device and a plurality of teeth are adapted to receive the pawl. The present invention additionally provides the benefit of limiting the amount of recoil of an expandable device by engaging a locking mechanism, thereby retaining the expanded diameter of the device.

36 Claims, 6 Drawing Sheets

U.S. PATENT DOCUMENTS

| | | |
|---|---|---|
| 5,049,132 A | 9/1991 | Shaffer et al. |
| 5,053,048 A | 10/1991 | Pinchuk |
| 5,059,166 A | 10/1991 | Fischell et al. |
| 5,059,178 A | 10/1991 | Ya |
| 5,059,211 A | 10/1991 | Stack et al. |
| 5,078,726 A | 1/1992 | Kreamer |
| 5,092,841 A | 3/1992 | Spears |
| 5,102,417 A | 4/1992 | Palmaz |
| 5,157,049 A | 10/1992 | Haugwitz et al. |
| 5,171,262 A | 12/1992 | MacGregor |
| 5,176,617 A | 1/1993 | Fischell et al. |
| 5,195,984 A | 3/1993 | Schatz |
| 5,197,978 A | 3/1993 | Hess |
| 5,213,580 A | 5/1993 | Slepian et al. |
| 5,234,456 A | 8/1993 | Silvestrini |
| 5,242,399 A | 9/1993 | Lau et al. |
| 5,286,254 A | 2/1994 | Shapland et al. |
| 5,292,512 A | 3/1994 | Schaefer et al. |
| 5,304,121 A | 4/1994 | Sahatjian |
| 5,314,688 A | 5/1994 | Kauffamn et al. |
| 5,342,348 A | 8/1994 | Kaplan |
| 5,342,621 A | 8/1994 | Eury |
| 5,344,426 A | 9/1994 | Lau et al. |
| 5,380,299 A | 1/1995 | Fearnot et al. |
| 5,383,892 A | 1/1995 | Cardon et al. |
| 5,383,928 A | 1/1995 | Scott et al. |
| 5,403,858 A | 4/1995 | Bastard et al. |
| 5,407,683 A | 4/1995 | Shively |
| 5,415,869 A | 5/1995 | Straubinger et al. |
| 5,419,760 A | 5/1995 | Narciso, Jr. |
| 5,439,446 A | 8/1995 | Barry |
| 5,439,686 A | 8/1995 | Desai et al. |
| 5,441,515 A | 8/1995 | Khosravi et al. |
| 5,441,745 A | 8/1995 | Presant et al. |
| 5,443,497 A | 8/1995 | Venbrux |
| 5,443,500 A | 8/1995 | Sigwart |
| 5,447,724 A | 9/1995 | Helmus et al. |
| 5,449,373 A | 9/1995 | Pinchasik et al. |
| 5,449,513 A | 9/1995 | Yokoyama et al. |
| 5,457,113 A | 10/1995 | Cullinan et al. |
| 5,460,817 A | 10/1995 | Langley et al. |
| 5,462,866 A | 10/1995 | Wang |
| 5,464,450 A | 11/1995 | Buscemi et al. |
| 5,464,650 A | 11/1995 | Berg et al. |
| 5,473,055 A | 12/1995 | Mongelli et al. |
| 5,499,373 A | 3/1996 | Richards et al. |
| 5,523,092 A | 6/1996 | Hanson et al. |
| 5,545,210 A | 8/1996 | Hess et al. |
| 5,551,954 A | 9/1996 | Buscemi et al. |
| 5,556,413 A | 9/1996 | Lam |
| 5,575,771 A | 11/1996 | Walinsky |
| 5,578,075 A | 11/1996 | Dayton |
| 5,578,075 A | 11/1996 | Dayton |
| 5,593,434 A | 1/1997 | Williams |
| 5,607,442 A | 3/1997 | Fischell et al. |
| 5,616,608 A | 4/1997 | Kinsella et al. |
| 5,617,878 A | 4/1997 | Taheri |
| 5,618,299 A | 4/1997 | Khosravi et al. |
| 5,624,411 A | 4/1997 | Tuch |
| 5,628,787 A | 5/1997 | Mayer |
| 5,643,314 A | 7/1997 | Carpenter et al. |
| 5,667,764 A | 9/1997 | Kopia et al. |
| 5,674,278 A | 10/1997 | Boneau |
| 5,697,971 A | 12/1997 | Fischell et al. |
| 5,707,385 A | 1/1998 | Williams |
| 5,713,949 A | 2/1998 | Jayaraman |
| 5,716,981 A | 2/1998 | Hunter et al. |
| 5,725,548 A | 3/1998 | Jayaraman |
| 5,725,549 A | 3/1998 | Lam |
| 5,733,330 A | 3/1998 | Cox |
| 5,733,925 A | 3/1998 | Kunz et al. |
| 5,741,293 A | 4/1998 | Wijay |
| 5,759,192 A | 6/1998 | Saunders |
| 5,766,239 A | 6/1998 | Cox |
| 5,769,883 A | 6/1998 | Buscemi et al. |
| 5,776,181 A | 7/1998 | Lee et al. |
| 5,800,507 A | 9/1998 | Schwartz |
| 5,817,152 A | 10/1998 | Birdsall et al. |
| 5,824,045 A | 10/1998 | Alt |
| 5,824,049 A | 10/1998 | Ragheb et al. |
| 5,827,322 A | 10/1998 | Williams |
| 5,837,313 A | 11/1998 | Ding et al. |
| 5,843,117 A | 12/1998 | Alt et al. |
| 5,843,120 A | 12/1998 | Israel et al. |
| 5,843,172 A | 12/1998 | Yan |
| 5,843,175 A | 12/1998 | Frantzen |
| 5,843,741 A | 12/1998 | Wong et al. |
| 5,853,419 A | 12/1998 | Imran |
| 5,855,600 A | 1/1999 | Alt |
| 5,868,781 A | 2/1999 | Killion |
| 5,873,904 A | 2/1999 | Ragheb et al. |
| 5,876,419 A | 3/1999 | Carpenter et al. |
| 5,882,335 A | 3/1999 | Leone et al. |
| 5,886,026 A | 3/1999 | Hunter et al. |
| 5,922,020 A | 7/1999 | Klein et al. |
| 5,922,021 A | 7/1999 | Jang |
| 5,957,971 A | 9/1999 | Schwartz |
| 5,964,798 A | 10/1999 | Imran |
| 5,968,092 A | 10/1999 | Buscemi et al. |
| 5,972,027 A | 10/1999 | Johnson |
| 5,976,182 A | 11/1999 | Cox |
| 5,984,957 A | 11/1999 | Laptewicz, Jr. et al. |
| 6,007,517 A | 12/1999 | Anderson |
| 6,017,363 A | 1/2000 | Hojeibane |
| 6,019,789 A | 2/2000 | Dinh et al. |
| 6,022,371 A | 2/2000 | Killion |
| 6,030,414 A | 2/2000 | Taheri |
| 6,042,606 A | 3/2000 | Frantzen |
| 6,056,722 A | 5/2000 | Jayaraman |
| 6,063,101 A | 5/2000 | Jacobsen et al. |
| 6,071,305 A | 6/2000 | Brown et al. |
| 6,083,258 A | 7/2000 | Yadav |
| 6,087,479 A | 7/2000 | Stamler et al. |
| 6,096,070 A | 8/2000 | Ragheb et al. |
| 6,099,561 A | 8/2000 | Alt |
| 6,120,535 A | 9/2000 | McDonald et al. |
| 6,120,847 A | 9/2000 | Yang et al. |
| 6,153,252 A | 11/2000 | Hossainy et al. |
| 6,156,062 A | 12/2000 | McGuinness |
| 6,159,488 A | 12/2000 | Nagler et al. |
| 6,174,326 B1 | 1/2001 | Kitaoka et al. |
| 6,193,746 B1 | 2/2001 | Strecker |
| 6,206,914 B1 | 3/2001 | Soykan et al. |
| 6,206,915 B1 | 3/2001 | Fagan et al. |
| 6,206,916 B1 | 3/2001 | Furst |
| 6,231,600 B1 | 5/2001 | Zhong |
| 6,240,616 B1 | 6/2001 | Yan |
| 6,241,762 B1 | 6/2001 | Shanley |
| 6,245,101 B1 | 6/2001 | Drasler et al. |
| 6,249,952 B1 | 6/2001 | Ding |
| 6,273,908 B1 | 8/2001 | Ndondo-Lay |
| 6,273,910 B1 | 8/2001 | Limon |
| 6,273,913 B1 | 8/2001 | Wright et al. |
| 6,280,411 B1 | 8/2001 | Lennox |
| 6,290,673 B1 | 9/2001 | Shanley |
| 6,293,967 B1 | 9/2001 | Shanley |
| 6,309,414 B1 | 10/2001 | Rolando et al. |
| 6,312,460 B2 | 11/2001 | Drasler et al. |
| 6,395,326 B1 | 5/2002 | Castro et al. |
| 6,451,051 B2 | 9/2002 | Drasler et al. |
| 6,475,237 B2 | 11/2002 | Drasler et al. |
| 6,506,411 B2 | 1/2003 | Hunter et al. |
| 6,506,437 B1 | 1/2003 | Harish et al. |
| 6,544,544 B2 | 4/2003 | Hunter et al. |

| | | | |
|---|---|---|---|
| 6,558,733 B1 | 5/2003 | Hossainy et al. | |
| 2001/0000802 A1 | 5/2001 | Soykan et al. | |
| 2001/0027340 A1 | 10/2001 | Wright et al. | |
| 2001/0034363 A1 | 10/2001 | Li et al. | |
| 2001/0044648 A1 | 11/2001 | Wolinsky et al. | |
| 2001/0044652 A1 | 11/2001 | Moore | |
| 2002/0002400 A1 | 1/2002 | Drasler et al. | |
| 2002/0005206 A1 | 1/2002 | Falotico et al. | |
| 2002/0007209 A1 | 1/2002 | Scheerder et al. | |
| 2002/0022876 A1 | 2/2002 | Richter et al. | |
| 2002/0038145 A1 | 3/2002 | Jang | |
| 2002/0072511 A1 | 6/2002 | New et al. | |
| 2002/0082679 A1 | 6/2002 | Sirhan et al. | |
| 2002/0094985 A1 | 7/2002 | Hermann et al. | |
| 2002/0123801 A1 | 9/2002 | Pacetti et al. | |
| 2002/0142039 A1 | 10/2002 | Claude | |
| 2002/0155212 A1 | 10/2002 | Hossainy | |
| 2004/0102836 A1 * | 5/2004 | Fischell et al. | 623/1.15 |

FOREIGN PATENT DOCUMENTS

| | | |
|---|---|---|
| DE | 2002 00 220 | 3/2002 |
| EP | 0 335 341 | 10/1989 |
| EP | 0 353 341 | 2/1990 |
| EP | 0 375 520 | 6/1990 |
| EP | 0 470 246 | 2/1992 |
| EP | 0 470 569 A1 | 2/1992 |
| EP | 0 566 245 A1 | 10/1993 |
| EP | 0 567 816 A1 | 11/1993 |
| EP | 0 627 226 A1 | 12/1994 |
| EP | 0 679 373 A2 | 11/1995 |
| EP | 0 734 698 A2 | 3/1996 |
| EP | 0 747 069 | 12/1996 |
| EP | 0 770 401 | 5/1997 |
| EP | 0 706 376 B1 | 6/1997 |
| EP | 0 897 700 A1 | 2/1999 |
| EP | 0 950 386 | 10/1999 |
| EP | 1 118 325 | 7/2001 |
| EP | 1 132 058 | 9/2001 |
| EP | 1 172 074 | 1/2002 |
| EP | 1 172 074 A2 | 1/2002 |
| EP | 1 223 305 | 7/2002 |
| EP | 1 236 478 | 9/2002 |
| FR | 764 794 A2 | 5/1934 |
| WO | WO 90/13332 | 11/1990 |
| WO | WO 91/10424 | 7/1991 |
| WO | WO 91/11193 | 8/1991 |
| WO | WO 91/12779 | 9/1991 |
| WO | WO 92/12717 | 8/1992 |
| WO | WO 92/15286 | 9/1992 |
| WO | WO 93/06792 | 4/1993 |
| WO | WO 94/21308 | 9/1994 |
| WO | WO 94/24961 | 11/1994 |
| WO | WO 95/03036 | 2/1995 |
| WO | WO 95/03795 | 2/1995 |
| WO | WO 95/24908 | 9/1995 |
| WO | WO 96/03092 | 2/1996 |
| WO | WO 96/25176 | 8/1996 |
| WO | WO 96/29028 | 9/1996 |
| WO | WO 96/32907 | 10/1996 |
| WO | WO 97/04721 | 2/1997 |
| WO | WO 98/08566 | 3/1998 |
| WO | WO 98/18407 | 5/1998 |
| WO | WO 98/19628 | 5/1998 |
| WO | WO 98/23228 | 6/1998 |
| WO | WO 98/23244 | 6/1998 |
| WO | WO 98/36784 | 8/1998 |
| WO | WO 98/58600 | 12/1998 |
| WO | WO 99/15108 | 4/1999 |
| WO | WO 99/16386 | 4/1999 |
| WO | WO 99/16477 | 4/1999 |
| WO | WO 99/44536 | 9/1999 |
| WO | WO 99/49928 | 10/1999 |
| WO | WO 99/55396 | 11/1999 |
| WO | WO 00/10613 | 3/2000 |
| WO | WO 00/45744 | 8/2000 |
| WO | WO 00/69368 | 11/2000 |
| WO | WO 00/71054 | 11/2000 |
| WO | WO 01/17577 | 3/2001 |
| WO | WO 01/45862 | 6/2001 |
| WO | WO 01/49338 | 7/2001 |
| WO | WO 01/87376 | 11/2001 |
| WO | WO 02/17880 | 3/2002 |
| WO | WO 02/26281 | 4/2002 |

OTHER PUBLICATIONS

Hwang, et al., "Physiological Transport Forces Govern Drug Distribution For Stent Based Delivery", Circulation, pp. 1-8, Aug. 17, 2001.

* cited by examiner

EXPANDABLE MEDICAL DEVICE WITH TAPERED HINGE

CLAIM OF PRIORITY

The present application claims priority to U.S. Provisional Patent Application Ser. No. 60/266,805 filed Feb. 5, 2001, the entirety of which is hereby incorporated by reference.

FIELD OF THE INVENTION

This invention relates to expandable medical devices, more particularly to an expandable medical device including a locking mechanism and low recoil after expansion from one diameter to a greater second diameter.

SUMMARY OF THE RELATED ART

In the past, permanent or biodegradable devices have been developed for implantation within a body passageway to maintain patency of the passageway. These devices are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665, 4,739,762, and 4,776,337). Known construction materials for use in stents include polymers, organic fabrics and biocompatible metals, such as, stainless steel, gold, silver, tantalum, titanium, and shape memory alloys such as Nitinol.

U.S. Pat. Nos. 4,733,665, 4,739,762, and 4,776,337 disclose expandable and deformable intraluminal vascular grafts in the form of thin-walled tubular members with axial slots allowing the members to be expanded radially outwardly into contact with a body passageway. After insertion, the tubular members are mechanically expanded beyond their elastic limit and thus permanently fixed within the body.

Many of the known stents display a large elastic recovery, known in the field as "recoil," after expansion inside a lumen. Large recoil necessitates over-expansion of the stent during implantation to achieve the desired final diameter. Over-expansion is potentially destructive to the lumen tissue and is known to cause higher rates of restenosis. Known stents of the type described above experience recoil of up to about 9 to 21% from maximum expansion.

Large recoil also makes it very difficult to securely crimp most known stents onto delivery catheter balloons. As a result, slippage of stents on balloons during intralumenal transportation, final positioning, and implantation has been an ongoing problem. Many ancillary stent securing devices and techniques have been advanced to attempt to compensate for this basic design problem. Some of the stent securing devices include collars and sleeves used to secure the stent onto the balloon.

Some materials have intrinsic properties that are beneficial in some aspects of stent design, and undesirable in other aspects. U.S. Pat. No. 5,545,210, for example, discloses a thin-walled tubular stent geometrically similar to those discussed above, but constructed of a nickel-titanium shape memory alloy ("Nitinol"). Martensitic Nitinol has a very low Young's Modulus, and a low, nearly horizontal "detwinning" stress plateau that provide an exceptionally large strain range before plastic deformation commences. When incorporated into conventional stent designs, these properties produce stents that have unusually good flexibility, deliverability, conformability and radiopacity, but also unacceptably high recoil and poor radial strength. For example, recoil of a typical design Nitinol stent ranges from 10% to 25%, typically about 12% to 16%.

One approach to remedying material-based recoil and radial strength problems is to employ locking or detent features in the stent design. A number of such locking stent designs have been proposed for conventional materials like stainless steel, but none has proven workable in practice. Many of the designs are simply impossible to manufacture on a small scale. More fundamentally, most of the designs fail to provide the basic mechanical requirements of a ratchet or detent mechanism: 1) two degree-of-freedom differential motion between the engaging elements, and 2) a restoring or spring force between the elements. It is relatively easy to provide these two elements in larger mechanisms comprised of discrete components, but much more difficult to provide this functionality while cutting all features into a very small, continuous, cylindrical surface.

FIG. 1 shows a typical prior art "expanding cage" stent design. The stent 10 includes a series of axial slots 12 formed in a cylindrical tube 14. Each axial row of slots 12 is displaced axially from the adjacent row by approximately half the slot length providing a staggered slot arrangement. The material between the slots 12 forms a network of axial struts 16 joined by short circumferential links 18. The cross section of each strut 16 remains constant or varies gradually along the entire length of the strut and thus the rectangular moment of inertia and the elastic and plastic section moduli of the cross section also remain constant or vary gradually along the length of the strut. Such a strut 16 is commonly referred to as a prismatic beam. Struts 16 in this type of design are typically 0.005 to 0.006 inches (0.127–0.1524 mm) wide in the circumferential direction. Strut thicknesses in the radial direction are typically about 0.0025 inches (0.0635 mm) or less to keep expansion forces within acceptable levels. However, most stent materials must be approximately 0.005 inches (0.127 mm) thick for good visibility on conventional fluoroscopic equipment. This high ratio of strut width to thickness, combined with the relatively high strut length and the initial curvature of the stent tubing combine to cause the instability and bucking often seen in this type of stent design. When expanded, the stent structure of FIG. 1 assumes the roughly diamond pattern commonly seen in expanded sheet metal.

Another stent described in PCT publication number WO 96/29028 uses struts with relatively weak portions of locally-reduced cross sections that on expansion of the stent act to concentrate deformation at these areas. However, as discussed above non-uniform expansion is even more of a problem when smaller feature widths and thicknesses are involved because manufacturing variations become proportionately more significant. The locally-reduced cross section portions described in this document are formed by pairs of circular holes. The shape of the locally reduced cross section portions undesirably concentrates the plastic strain at the narrowest portion. This concentration of plastic strain without any provision for controlling the level of plastic strain makes the stent highly vulnerable to failure.

U.S. Pat. No. 6,241,762, entitled "EXPANDABLE MEDICAL DEVICE WITH DUCTILE HINGES" filed Oct. 10, 1998 and assigned to Conor Medsystems Inc., is incorporated herein by reference in its entirety. This patent discloses a stent design that provides a stent with large, non-deforming strut and link elements, which can contain holes without compromising the mechanical properties of the strut or link elements, or the device as a whole. Further, these holes may serve as large, protected reservoirs for delivering various beneficial agents to the device implantation site.

In view of the drawbacks of prior art stents, it would be advantageous to have an expandable medical device with low radial recoil and high radial force (circumferential crush strength) independent of the intrinsic properties of the material of fabrication.

It would further be advantageous to have a tissue-supporting device that could be expanded to a range of final diameters independent of the means of expansion or the force levels applied.

It would also be desirable to control the maximum material strain to a desired level wherein when the expandable medical device is deployed the material remains below its elastic limit, and may be expanded to a greater diameter if necessary without plastically deforming the material.

SUMMARY OF THE PRESENT INVENTION

The present invention makes novel use of hinges to provide both the spring force and two degrees-of-freedom motions required for a true self-locking expandable medical device design. In addition to that above the present invention provides a novel expandable medical device that is capable of self-expansion or expansion through the use of a balloon catheter or similar device. Further still, the expandable medical device according to the present invention may be utilized to deliver a beneficial agent to the area adjacent to the expanded medical device.

In accordance with one aspect of the present invention there is provided an expandable medical device including a plurality of elongated beams. The plurality of elongated beams are joined together to form a substantially cylindrical device. The cylindrical device is expandable from a cylinder having a first diameter to a cylinder having a second diameter, the plurality of the elongated beams having a beam width in a circumferential direction. A plurality of hinges connecting the elongated beams have a hinge width, wherein the hinge width is smaller than the beam width. A pawl is disposed adjacent to and substantially parallel to the hinge prior to expansion of the medical device and a plurality of teeth are adapted to receive the pawl.

In accordance with another aspect of the present invention there is provided an expandable medical device including a cylindrical tube and a plurality of axial slots formed in the cylindrical tube in an arrangement to define a network of elongated struts, wherein each of the elongated struts are radially displaced from adjacent struts, and each elongated strut further includes at least one tooth disposed thereupon. A pawl formed between the elongated struts has a distal end adapted to be received by the tooth. A plurality of hinges formed between the elongated struts allow the cylindrical tube to be expanded from a first diameter to a second diameter by bending of the hinges and engaging the distal end of the pawl with the tooth.

In accordance with another aspect of the present invention there is provided an expandable medical device including, a cylindrical expandable body of Nitinol and a locking feature for locking the expanded body in an expanded position, wherein the locking mechanism prevents recoil of the expanded body of greater than 5 percent.

In accordance with another aspect of the present invention there is provided a method of processing an expandable medical device, the method including the steps of fabricating a cylindrical expandable medical device from martensitic Nitinol, where the expandable medical device is fabricated with a first unexpanded diameter. Expanding the cylindrical expandable medical device to an expanded second diameter, wherein deformation during expansion is confined to a hinge and the deformation is below the elastic limit of the material. Processing the expandable medical device, and restoring the expandable medical device to the unexpanded first diameter by applying heat to the expandable medical device.

In accordance with another aspect of the present invention there is provided an expandable medical device, the expandable medical device includes a plurality of elongated beams and a plurality of hinges. The plurality of elongated beams joined together to form a substantially cylindrical device that is expandable to form a cylinder having a first diameter to a cylinder having a second diameter. The plurality of the elongated beams have a beam width in a circumferential direction, the beam width of the elongated members being less than the width of the hinges. The expandable medical device further including an internal self locking mechanism.

In accordance with yet another aspect of the present invention there is provided a method of constructing an expandable medical device. The method including the steps of fabricating an expandable medical device from a cylindrical member, the expandable medical device is formed having a first unexpanded diameter, retracting the expandable medical device to an unexpanded second diameter where deformation during retraction is confined to a hinge portion of the expandable medical device, and retaining the expandable medical device in the unexpanded diameter.

BRIEF DESCRIPTION OF THE DRAWINGS

The invention will now be described in greater detail with reference to the preferred embodiments illustrated in the accompanying drawings, in which like elements utilize like reference numerals, and wherein.

DETAILED DESCRIPTION OF PREFERRED EMBODIMENTS

Figure 1:
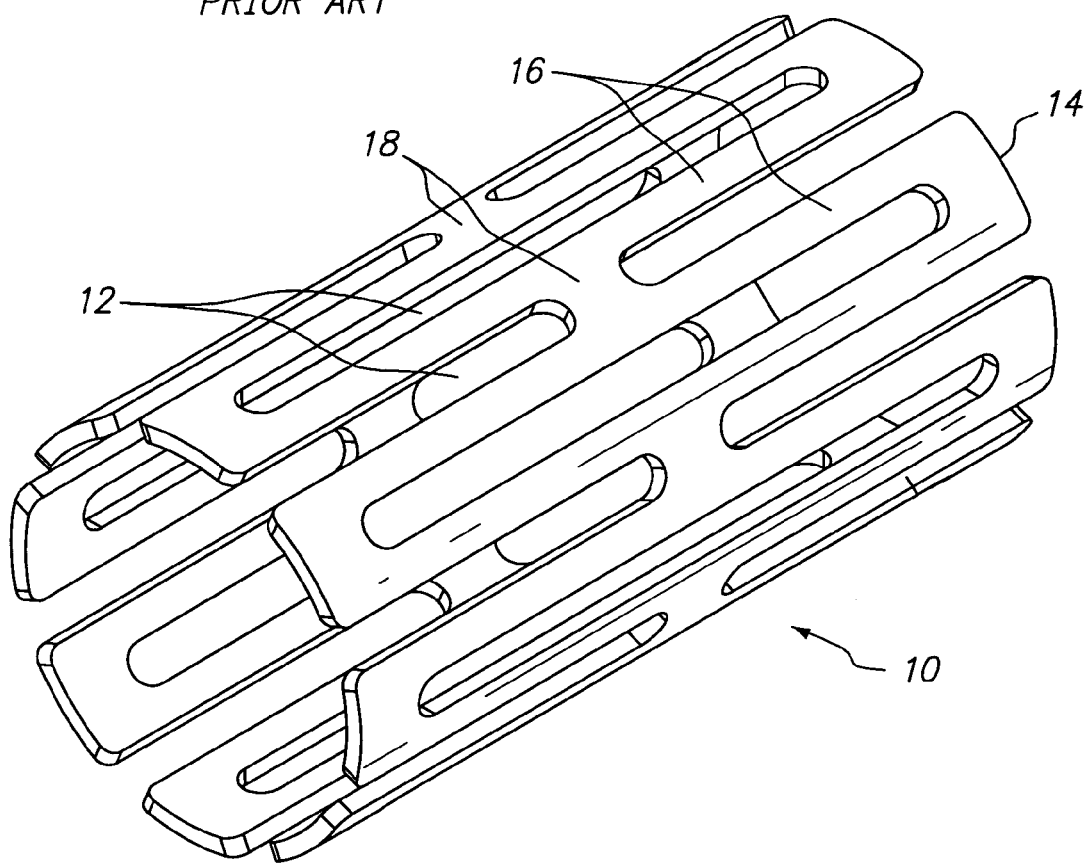
FIG. 1 is an isometric view of a prior art tissue-supporting device.
Figure 2A:
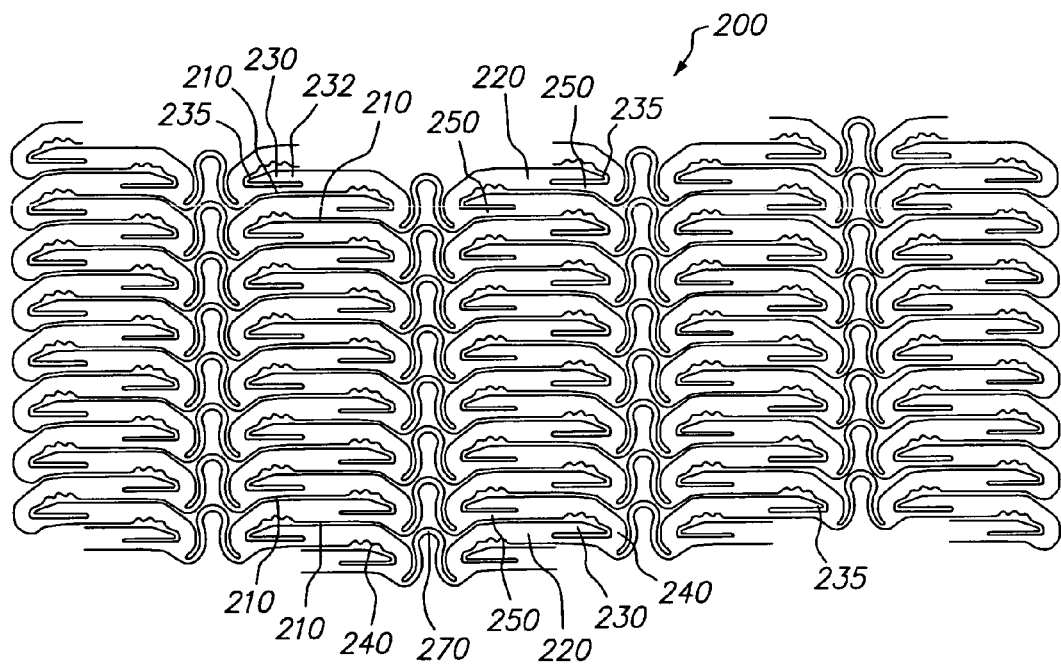
FIG. 2A is a planar view of a representative portion of an unexpanded tissue-supporting device in accordance with one embodiment of the invention.
Figure 2B:
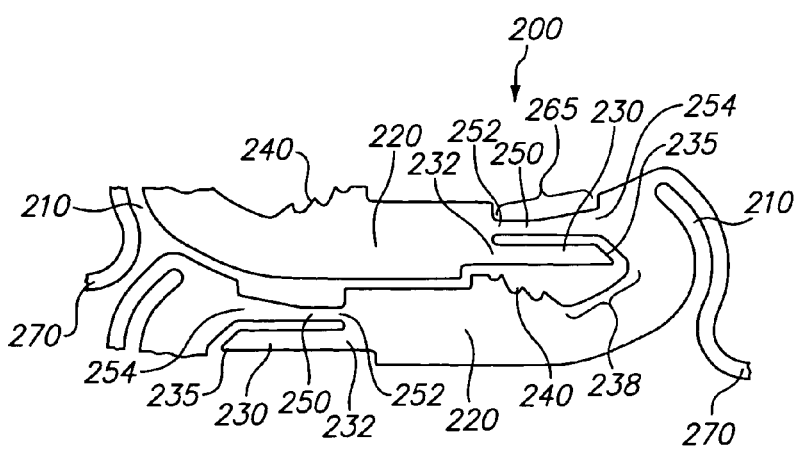
FIG. 2B is a sectional planar view of a single expanding member in accordance with the present invention.

Referring now to FIGS. 2A and 2B, there is shown a planar view of a representative portion of an unexpanded tissue-supporting medical device 200. The expandable medical device 200 includes a series of axial slots 210 formed in a cylindrical tube (not shown). Each axial slot 210 is displaced radially from the slots in the adjacent rows of slots by approximately 0.010 inches. The plurality of axial slots 210 define a plurality of elongated beams 220. The plurality of elongated beams 220 are interconnected by a hinge 250 disposed at one end and a locking area disposed at the other end. A U-shaped link 270 interconnects adjacent rows of beams 220.

The elongated beam 220 further includes a pawl 230 having a distal end 235 disposed at one end of the elongated beam 220 and a plurality of teeth 240 disposed at the other end opposite the pawl 230. The elongated beam 220 further includes a hinge 250 adjacent the pawl 230. The hinge 250 further contains a first end 252 and a second end 254 defining a section 265, wherein the section 265 between the first end 252 and the second end 254 is designed where it will act as a stress/strain concentration area. Specifically, the hinge 250 contains a first portion extending along about ⅓ of the length of the hinge 250 and a second section gradually tapering, extending about ⅔ of the length of the hinge 250. It is contemplated that other ratios may be utilized as well as other geometries in order to confine the maximum stress/strain to the hinge section 265. Furthermore, the length and width of the hinge can be adjusted to confine the maximum strain in the hinge 250, to some desired value at the maximum required bend radius of the hinge 250.

For example, if the maximum desired bend angle of the hinge 250 was set at ninety (90) degrees, and the minimum hinge width was fixed at about 0.002 inches, a hinge length could be determined which would guarantee that the maximum strain in the hinge 250 was well below the elastic limit of some specified material. For example, the expandable medical device could be manufactured of materials such as titanium, stainless steel, polymers, or preferably a Nitinol alloy, wherein the Nitinol alloy may be either martensitic or austenitic super-elastic.

With reference to the drawings and the discussion, the width of any feature is defined as its dimension in the circumferential direction of the cylinder. The length of any feature is defined as its dimension in the axial direction of the cylinder. The thickness of any feature is defined as the wall thickness of the cylinder.

When manufactured as a continuous array as shown in FIG. 2, the distal end 235 of the pawl 230 is adjacent to the teeth 240 of the adjacent elongated member 220.

Figure 3A:
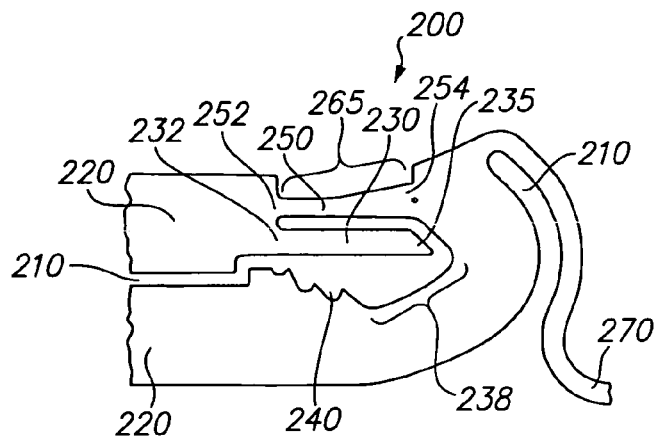
FIG. 3A is a detail view of the expandable medical device of FIG. 2 undergoing sequential expansion.
Figure 3B:
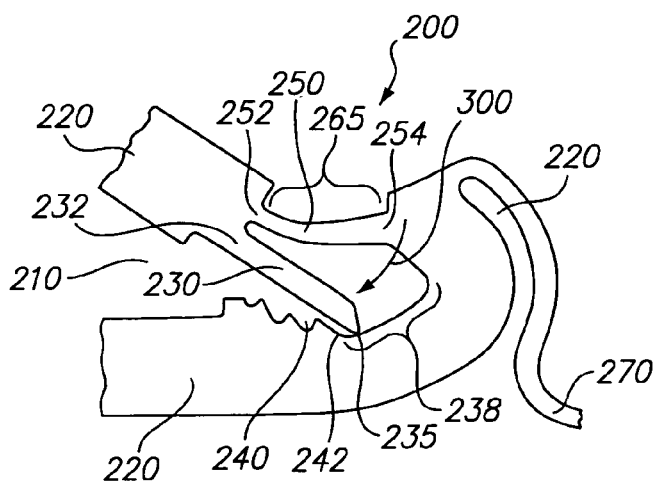
FIG. 3B is a detail view of the expandable medical device of FIG. 2 undergoing sequential expansion.
Figure 3C:
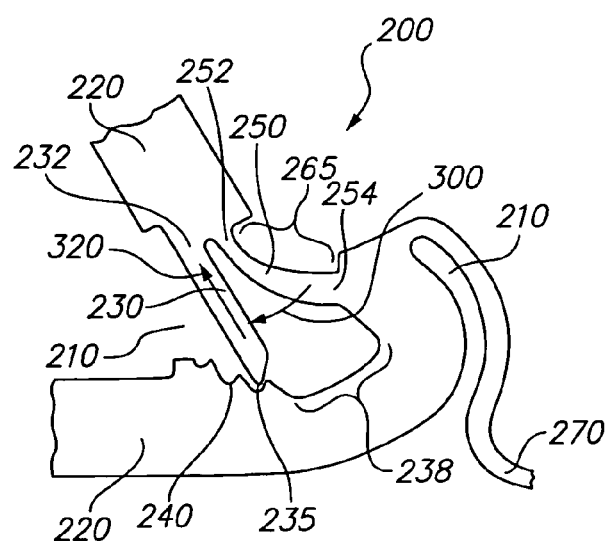
FIG. 3C is a detail view of the expandable medical device of FIG. 2 undergoing sequential expansion.

Referring now to FIGS. 3A through 3C there is shown a plan view of a section of the expandable medical device 200 as the device is deployed. The expandable device 200 may be expanded radially by placing an appropriate device, such as a balloon catheter within the inner diameter of the expandable device 200 and expanding the balloon catheter until the expandable device has been expanded to a desired diameter.

Additionally the expandable medical device 200 may be constructed having a plurality of apertures for receiving a beneficial agent, which may be released after insertion within a patient. For a more detailed description of the apparatus and methods for delivering a beneficial agent, See co-pending U.S. Patent application Ser. No. 09/649,217 entitled "Expandable Medical Device With Ductile Hinges", filed Aug. 28, 2000 which is hereby incorporated by reference in its entirety.

Furthermore, the expandable device 200 may be constructed of materials such as polymers, biodegradable materials, or combinations of polymers, biodegradable materials and Nitinol. The locking mechanism of the present invention provides the ability to decrease the recoil and increase the radial strength of expandable devices constructed of these materials, thereby allowing an expandable device to be constructed of these materials.

The polymer and/or the biodegradable materials may be further adapted to receive a beneficial agent that may then be eluted after the expandable device is deployed within a patient. For example, the beneficial agent may be contained within the polymer or biodegradable material, in which the characteristics of the polymer or biodegradable material control the release rate of the beneficial agent after the expandable device is deployed within a patient.

As shown in FIG. 3A, a partial section of the expandable device 200 is shown. As described in detail above, the expandable device 200 includes a plurality of elongated members 220, spaced apart by radial slots 210. The elongated members have a pawl 230 disposed on one end thereof and a plurality of teeth 240 disposed on the other, and a hinge 250 adjacent to the pawl 230. The plurality of elongated members 220 are joined together by the hinge 250 and the locking configuration. In an unexpanded state, as shown in FIG. 3A, the pawl 230 disposed at one end of an elongated member 220 is substantially parallel to hinge 250. Further still the distal end 235 of the pawl 230 is designed having a 'chisel' shape adapted for being received by at least one of the plurality of teeth 240 on the adjacent substantially parallel elongated member 220.

Referring now to FIG. 3B, there is shown the partial section of the expandable device 200 having been expanded to a second partially expanded diameter. As indicated by arrow 300 a general rotational motion is achieved by pawl 230 as the diameter of the expandable device 200 is increased and hinge 250 bends. As shown, the locus of points drawn out by distal tip 235 of the pawl 230 as it rotates describes a non-circular arc. The hinge 250 bends initially about a pre-determined point within the region 265 as shown in FIG. 3B. The predetermined bending point is determined by narrowing the width of the hinge 250 within the section 265 as defined by the first end 252 and the second end 254 of the hinge 250. As shown FIG. 3B, as the pawl rotates during expansion of the device from an unexpanded state as shown in FIG. 3A to a partially expanded state as shown in FIG. 3B the pawl 230 is no longer substantially parallel to the hinge 250 due to the bending of the hinge 250.

If the expandable device of FIG. 3B were fabricated of an martensitic Nitinol (shape memory) alloy, it could at this point be fully restored to the configuration of FIG. 3A by heating the device above its transformation temperature. This is possible because the pawl has not yet engaged the first tooth in the adjacent strut, and the material is never stressed beyond its elastic limit. This feature is useful for intermediate fabrication steps, for example electropolishing, where the device can be expanded to an "open" configuration for more effective polishing and then thermally restored to a smaller diameter for mounting on a delivery system.

Figure 4:
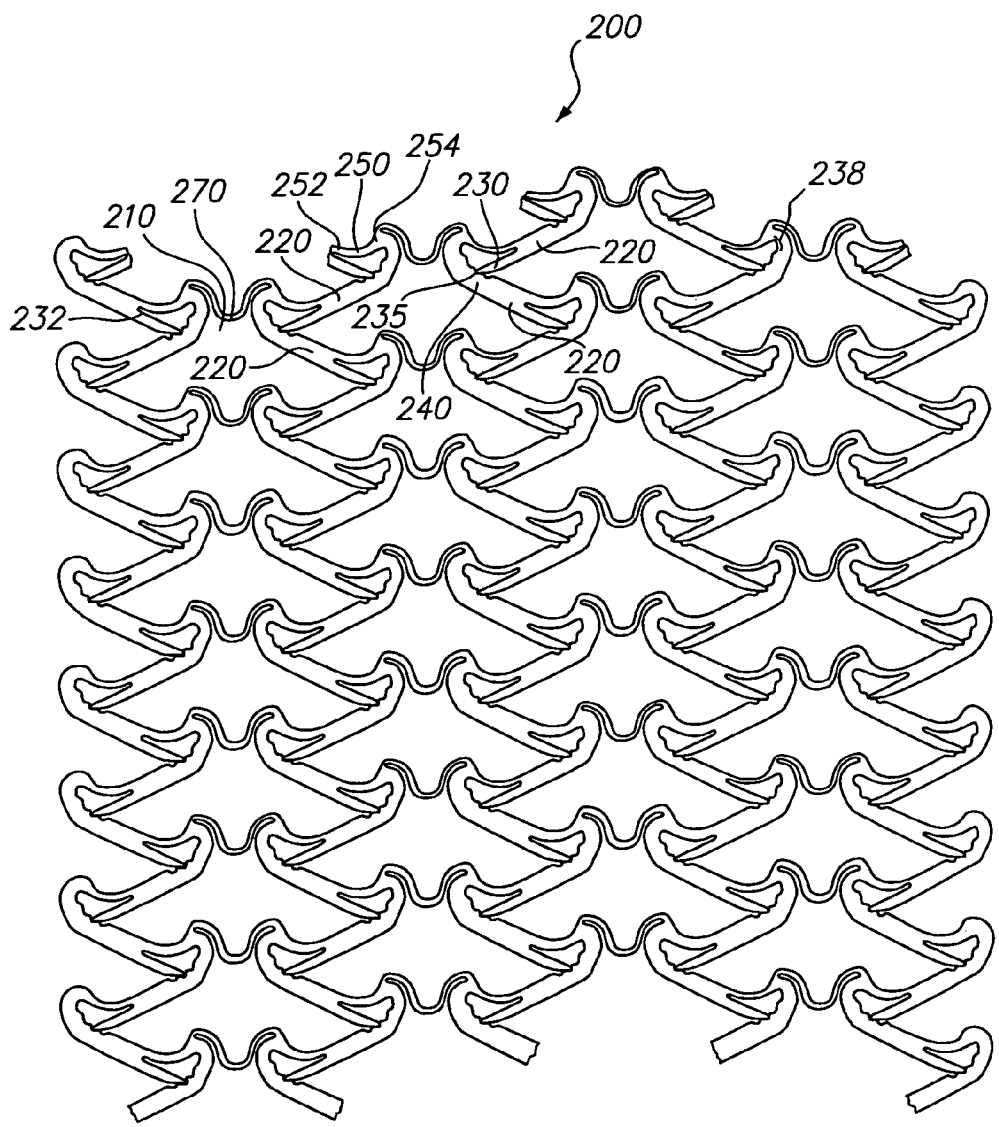
FIG. 4 is a planar view of the expandable device of the present invention in an expanded and locked state.

Referring now to FIG. 3C, there is shown the section of the expandable medical device 200 in an expanded state during engagement of the locking mechanism. As shown, a significant curvature develops in the hinge 250, specifically in the section 265. As this curvature occurs, the pawl 230 and the distal end 235 of the pawl 230 become capable of both continued angular deflection, as indicated by arrow 300, and also a linear motion along the axis of the pawl 230, as indicated by arrow 320. The angular motion 300 and the linear motion 320 are both possible in this region because the axis of the pawl 230 is no longer directly aligned with the now-curved, centroidal axis of the hinge 250. Rather, the motion of the pawl 230 along its own axis requires only additional bending of the hinge 250 near second end 254 of the hinge 250. This ability of the hinge 250 to provide both the rotational motion 300 and the axial motion 320 allows the distal tip 235 of the pawl 230 to follow the contour of the teeth 240 without local plastic yielding of either feature. Additionally, the elastic energy stored in the hinge 250 provides a means for creating a spring return force (not shown) that can be resolved at the distal tip 235 of the pawl into components parallel and perpendicular to the axis of the pawl. When the expansion device has positioned the distal tip 235 of the pawl 230 beyond one of the locking teeth 240, and the expansion device is then withdrawn, these spring return forces force the distal tip 235 to contact the locking tooth 240, thereby locking the expandable device 200 into an expanded state as shown in FIG. 4. The mating faces of the distal tip 235 and the locking tooth 240 are contoured according to well-known techniques to insure that forces that are externally applied to the tissue-supporting device 200 act to further lock the features in position. Furthermore, throughout the description reference is made to the teeth 240, it shall be understood that this reference should not be considered limiting. For example, the teeth 240 may comprise many different geometrical shapes, which are adapted to receive the distal end 235 of the pawl 230. For example, the teeth 240 may be comprised of depressions adapted to receive the distal end 235 of the pawl 230. Thus, the teeth 240 as shown and described are not to be considered limiting and are exemplary only; it is contemplated that the teeth 240 as well as the distal end 235 of the pawl 230 may comprise many different shapes as shall be apparent to one skilled in the art.

For example, when the expandable medical device 200, as described above, is fabricated from a Nitinol alloy, an exceptionally large sub-plastic strain range is available, and very large deformations are possible without exceeding the material's elastic limit. If the locking teeth of the expandable device 200 were absent, the device could be restored to its original shape by heating, since it is never plastically deformed during the expansion sequence of FIG. 3.

Additionally, the hinge 250 may be contoured as described above in order to control the bending pattern of the hinge 250 and thus the motion of the pawl during the bend sequence. For example, when the width of the hinge is narrowest near the pawl proximal end 232 of the pawl 230, the hinge tends to bend in this area first. As a result, the instant center of rotation of the pawl is initially closer to the proximal end 232 of the pawl 230, and the arc traced by the distal tip 235 of the pawl 230 quickly passes through the region 238 as indicated in FIGS. 3A–3C. This may be visualized by imagining the limiting case of a simple pivot point located at end 252 of hinge 250 the arc traced by distal tip 235 would in this case be circular, and the initial motion of the tip 235 would be orthogonal to the axis of pawl 230 (i.e., downward, or directly toward the adjacent strut 220). The second limiting case would correspond to a pivot point at the other end 254 of hinge 250. The arc traced by distal tip 235 would again be circular, but in this case, the initial motion of the tip 235 would be parallel to the axis of pawl 230, the tip of the pawl would move away from contact with adjacent strut 220 from the outset, and no locking would be possible with teeth 240 of the adjacent strut 220. By contouring the shape of hinge 250 between these extremes, the relative motion of pawl 230 with respect to adjacent strut 220 containing teeth 240 may be optimized.

Figure 3D:
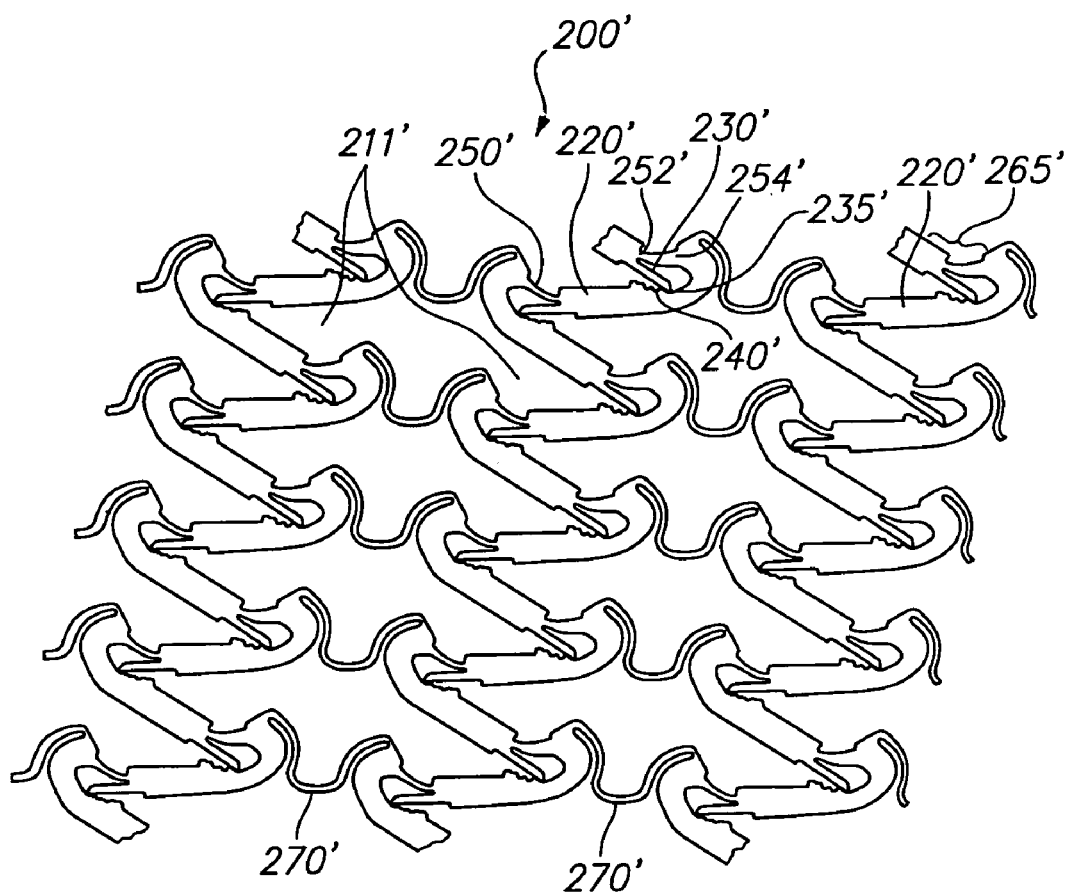
FIG. 3D is a detail view of an alternative embodiment of the expandable medical device in accordance with the present invention.

Referring now to FIG. 3D there is shown an exemplary alternative embodiment of the expandable device according to the present invention. Referring to FIG. 3D there is shown a planar view of a representative portion of an unexpanded expandable medical device 200' in accordance with an alternative embodiment of the present invention. The expandable medical device 200' includes a series of spaced apart areas 211' formed within a cylindrical tube (not shown). The cylindrical tube being constructed of superelastic Nitinol alloy, wherein the cylindrical tube defines a first diameter of the expandable medical device 200'. By utilizing a superelastic Nitinol alloy for the construction of the expandable medical device 200', the expandable medical device 200' can be formed in a semi-expanded state as shown in FIG. 3D. Each spaced apart area 211' defines a plurality of elongated beams 220'. The plurality of elongated beams are interconnected by a hinge 250' disposed at one end and a locking area disposed at the other end. A U-shaped link 270' interconnects adjacent rows of beams 220'. As shown, the elongated beam 220' further includes a pawl 230' having a distal end 235' disposed at one end of the elongated beam 220' and a plurality of teeth 240' disposed at the other end opposite the pawl 230'. The hinge 250' further includes a first end 252' and a second end 254' defining a section 265', wherein the section 265' between the first end 252' and the second end 254' is designed where it will act as a stress/strain concentration area. Specifically, the hinge 250' contains a first portion extending along about ⅓ of the length of the hinge 250' and a second section gradually tapering, extending about ⅔ of the length of the hinge 250'. It is contemplated that other ratios may be utilized as well as other geometries in order to confine the maximum stress/strain to the hinge section 265'. Furthermore, the length and width of the hinge can be adjusted to confine the maximum strain in the hinge 250' to some desired value at the maximum required bend radius of the hinge 250'.

As shown in FIG. 3D, it can be seen that expandable medical device 200' is constructed in a semi-expanded state wherein the distal end 235' of the pawl 230' has not been engaged with the teeth 240'. By constructing the expandable medical device 200' in this manner enables the expandable medical device 200' to be reduced to a diameter less than the initial fabrication diameter of the cylindrical tube. By reducing the diameter of the expandable medical device 200' it can be loaded onto a delivery device such as any of the delivery catheters available from many different manufacturers. The expandable medical device 200' may be retained in a compressed state through the use a removable sleeve or similar device such as those known to one skilled in the art.

In use, the expandable medical device 200' would be placed within a patient's artery in a desired location, the sleeve or retaining device would be removed and/or activated wherein the expandable medical device 200' would then expand to the first diameter of the cylindrical tube which is the origional fabrication diameter of the expandable medical device 200'. The expandable medical device 200' will automatically expand to this first diameter without the need to utilize any expanding means such as an inflatable balloon disposed within the inner diameter of the expandable medical device. The expandable medical device 200' can then be further expanded to engage the pawl and locking teeth, thereby locking the expandable medical device in an expanded position at a third diameter.

Figure 5:
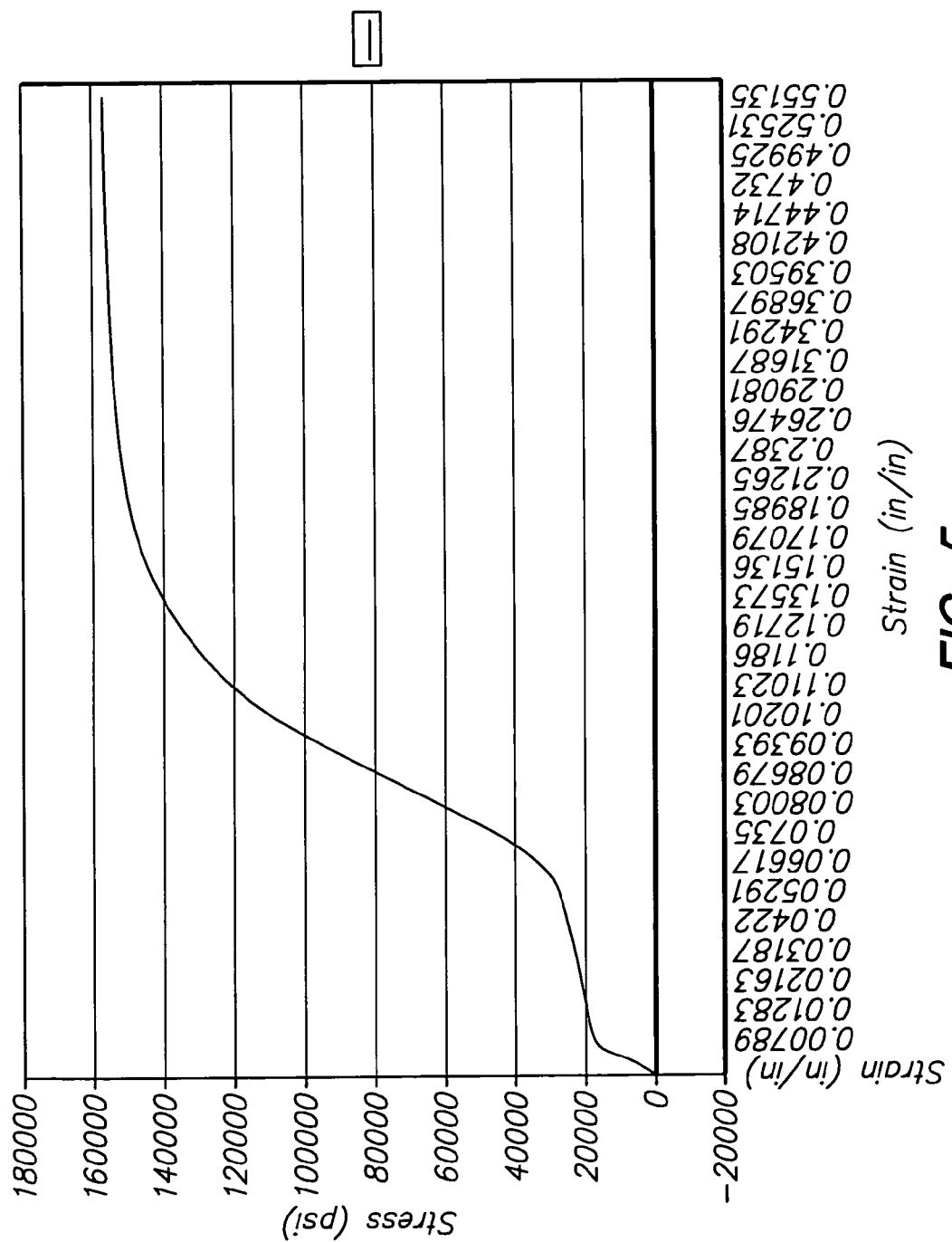
FIG. 5 is a stress/strain curve of a martensitic Nitinol alloy illustrating the extended sub-plastic strain range and the horizontal "de-twinning plateau" of the material.

Throughout this description reference has been made to materials that may be utilized in the construction of the expandable device 200. In a preferred embodiment the expandable device 200 is constructed of Nitinol alloy. Referring now to FIG. 5, there is shown a stress/strain diagram of a martensitic Nitinol alloy that may be utilized in the construction of the expandable device 200. As shown in FIG. 5, the alloy 500 has a very low Young's Modulus, a low, nearly horizontal "de-twinning" stress plateau, and a 0.2% offset yield stress (elastic limit) of approximately 108 ksi. These characteristics provide an exceptionally large strain range before plastic deformation commences.

This exceptionally large strain range, when incorporated in the present invention, provides the benefit of a device that may be expanded from an initial diameter to a range of pre-determined diameters, the range of pre-determined diameters depend only on the geometry of the locking elements and not on the forces applied by an expansion means. By utilizing the elastic and "de-twinning" strain ranges of Nitinol, the expandable device 200 of the present invention remains below its elastic limit before, during, and after the deployment of the device within an appropriate location.

Furthermore, the locking mechanism 280, which includes the pawl 230, and the teeth 240, provides the ability to decrease the 'recoil' of the expandable device 200. As described in detail above, stents that have been manufactured of Nitinol exhibit recoil percentages greater than many other suitable materials, thus Nitinol has not been commonly utilized for the construction of expandable stents. The locking mechanism 280 of the present invention reduces the amount of recoil associated with expandable Nitinol devices. For example, the expandable device of the present invention exhibits recoil between about 2% and about 8%, and preferably between about 4% and about 6%. Additionally, due to the locking mechanism 280 of the present invention, other materials may be utilized in the construction of expandable medical devices that could not have been utilized before due to large recoil percentages of the material. For example, an expandable device may be constructed of a polymer, a biodegradable material, or a combination of a polymer and Nitinol.

A further feature of the expandable devices in accordance with the present invention is the reduced necessity to over-expand the device in service. Prior art stents, and in particular nitinol stents often required over-expansion during deployment to achieve an acceptable "minimum lumen diameter," or MLD, post procedure. This is undesirable for several reasons, including the risk of collateral damage to the lumen, including perforation, and increased risk of long-term restenosis of the artery. Once the desired MLD has been achieved in the present invention, however, that diameter can be sustained without additional expansion due to the locking mechanism. At the same time, the present invention easily permits additional expansion, if required: due to the plurality of teeth 240 provided on one end of the elongated member 220, the distal end 235 of the pawl 230 may be advanced to engage another one of the teeth 240, thereby increasing the overall expanded diameter of the expandable device 200.

In addition to the embodiments above, it is contemplated that the expandable device 200/200' may further include a means for retaining and delivering a beneficial agent. For example, the beams 220 may include a plurality of apertures (not shown) disposed there through, in which a beneficial agent may be disposed. After the expandable device 200 has been placed within a vessel/artery, the beneficial agent is released from the apertures in a controlled fashion. Furthermore, it is contemplated that the expandable device 200 may be constructed from many different types of materials, such as, polymers, biodegradable materials, biocompatible materials, super-elastic alloys or a composite of any of the materials.

Still further, constructing the expandable medical device 200' of superelastic Nitinol alloy further increases the safety of the expandable medical device. That is, the locking mechanism of the expandable medical devices in accordance with the present invention provides increased resistance to circumferential compression forces. Examples of such circumferential forces are artery spasms and elasticity of the artery wall or recoil as described above. Additionally, constructing the expandable medical device of superelastic Nitinol alloy allows the device to recover from deformations caused by forces applied perpendicular to the longitudinal axis of the device, such as flat plate crushing forces. For example, the expandable medical device 200' may be utilized in a peripheral location such as the carotid artery, where the medical device is more vulnerable to being crushed by an external force or blow to the patient's neck. A conventional stainless steel stent cannot be utilized in this location because once deformed the stent will not return to its expanded state, thus potentially blocking the artery of which it was intended to support. By contrast, the expandable medical device 200' in accordance with the present invention will return to its expanded and locked state if it is crushed due to an applied force because of the material properties of superelastic nitinol and the geometry of the expandable medical device 200'.

While the invention has been described in detail with reference to the preferred embodiments thereof, it will be apparent to one skilled in the art that various changes and modifications can be made and equivalents employed, without departing from the present invention.

What is claimed is:

1. An expandable medical device comprising:
    a plurality of elongated beams, the plurality of elongated beans joined together to form substantially cylindrical elements which are expandable from cylinders having a first diameter to cylinders having a second diameter, the plurality of elongated beams having a beam width in a circumferential direction and wherein adjacent elongated beams form substantially V-shapes when the cylinders are at the second diameter;
    a plurality of flexible links interconnecting the substantially cylindrical elements; and
    a plurality of hinges connecting the elongated beams and positioned away from apexes of the substantially V-shapes, wherein deformation during expansion is confined substantially to the hinges and the flexible links, wherein the plurality of hinges each have a tapered portion such that an end of each hinge closer to the apex of the substantially V-shapes formed by the adjacent elongated beams has a width which is greater than a width of the hinge at an opposite end, and the tapered portion has a length longer than a non-tapered portion of the hinge.

2. The device of claim 1, wherein the plurality of hinges taper substantially linearly.

3. The device of claim 1, wherein the non-tapered portion extends along about ⅓ of the length of the hinge and the tapered portion extends along about ⅔ of the length of the hinge.

4. The device of claim 1, wherein during expansion the hinges experience deformation below their elastic limit.

5. The device of claim 1, wherein during expansion a structure adjacent the hinges experiences at least two degrees of freedom of motion.

6. The device of claim 1, wherein the plurality of hinges are tapered with the hinge widths, hinge length, and taper adjusted to achieve a desired value of the maximum strain along the hinges.

7. The device of claim 1, wherein the taper is substantially constant along a length of about ⅔ of a length of the hinge.

8. The device of claim 1, wherein the taper extends along a length of about ⅔ of a length of the hinge.

9. The device of claim 1, comprising a pawl disposed adjacent to the hinge and a plurality of teeth adapted to receive the pawl in a locking configuration.

10. The device of claim 9, wherein during expansion, the pawl experiences at least two degrees of freedom of motion.

11. The device of claim 1, wherein the device is laser-cut.

12. The device of claim 1, wherein the elongated beams further include a plurality of apertures disposed therein and a beneficial agent disposed within the apertures.

13. The device of claim 1, wherein a recoil of the medical device after expansion to the second diameter is less than about eight percent.

14. The device of claim 1, wherein a recoil of the medical device after expansion to the second diameter is less than about five percent.

15. The device of claim 1, wherein the device is manufactured of a biodegradable material.

16. The device of claim 1, wherein the device is manufactured of Nitinol, polymer, or a composite of polymer and Nitinol.

17. An expandable medical device according to claim 1, wherein the width of the hinge closest to the apex of the substantially V-shapes is smaller than the beam width.

18. An expandable medical device according to claim 1, wherein the hinges are coaxial with an adjacent elongated beam when the stent is in the first diameter.

19. An expandable stent comprising:
a plurality of elongated beams joined together to form a substantially cylindrical elements which are expandable from cylinders having a first diameter to cylinders having a second diameter, wherein adjacent ones of the plurality of elongated beams form substantially V-shapes when the cylinders are at the second diameter;
a plurality of flexible links interconnecting the substantially cylindrical elements; and
a plurality of hinges connecting the elongated beams and positioned away from apexes of the substantially V-shapes, wherein deformation during expansion is confined substantially to the hinges and the flexible links, wherein the plurality of hinges each includes a tapered portion such that an end of each hinge closer to the apex of the substantially V-shapes formed by the adjacent elongated beams has a width which is greater than a width of the hinge at an opposite end, and wherein substantially the entire tapered portion of the hinge deforms during expansion of the cylinder from the first diameter to the second diameter.

20. The stent of claim 19, wherein the tapered portion tapers substantially linearly.

21. The stent of claim 19, wherein a non-tapered portion of the hinge extends along about ⅓ of the length of the hinge and the tapered portion of the hinge extends along about ⅔ of the length of the hinge.

22. The stent of claim 19, wherein during expansion the hinges experience deformation below their elastic limit.

23. The stent of claim 19, wherein during expansion a structure adjacent the hinges experiences at least two degrees of freedom of motion.

24. The stent of claim 19, wherein the plurality of hinges are tapered with the hinge widths, hinge length, and taper adjusted to achieve a desired value of the maximum strain along the hinges.

25. The stent of claim 19, wherein the taper is substantially constant along a length of about ⅔ of a length of the hinge.

26. The stent of claim 19, wherein the taper extends along a length of about ⅔ of a length of the hinge.

27. The stent of claim 19, comprising a pawl disposed adjacent to the hinge and a plurality of teeth adapted to receive the pawi in a locking configuration.

28. The stent of claim 27, wherein during expansion, the pawl experiences at least two degrees of freedom of motion.

29. The stent of claim 19, wherein the device is laser-cut.

30. The stent of claim 19, wherein the elongated beams further include a plurality of apertures disposed therein and a beneficial agent disposed within the apertures.

31. The stent of claim 19, wherein a recoil of the medical device after expansion to the second diameter is less than about eight percent.

32. The stent of claim 19, wherein a recoil of the medical device after expansion to the second diameter is less than about five percent.

33. The stent of claim 19, wherein the device is manufactured of a biodegradable material.

34. The stent of claim 19, wherein the device is manufactured of Nitinol, polymer, or a composite of polymer and Nitinol.

35. The stent of claim 19, wherein the width of the hinge closest to the apex of the substantially V-shapes is smaller than the beam width.

36. The stent of claim 19, wherein the hinges are axially aligned with an adjacent elongated beam when the stent is in the first diameter.

* * * * *